US012434054B2

(12) United States Patent
Obrist et al.

(10) Patent No.: US 12,434,054 B2
(45) Date of Patent: Oct. 7, 2025

(54) URINARY PUMPING DEVICE

(71) Applicant: UNIVERSITÄT BERN, Bern (CH)

(72) Inventors: Dominik Obrist, Suhr (CH); Francesco Clavica, Derendingen (CH); Fiona Burkhard, Bern (CH); Marc Schneider, Steffisburg (CH); Lukas Bereuter, Bern (CH)

(73) Assignee: UNIVERSITÄT BERN, Bern (CH)

( * ) Notice: Subject to any disclaimer, the term of this patent is extended or adjusted under 35 U.S.C. 154(b) by 933 days.

(21) Appl. No.: 17/426,465

(22) PCT Filed: Jan. 29, 2020

(86) PCT No.: PCT/EP2020/052115
§ 371 (c)(1),
(2) Date: Jul. 28, 2021

(87) PCT Pub. No.: WO2020/157105
PCT Pub. Date: Aug. 6, 2020

(65) Prior Publication Data

US 2022/0096830 A1 Mar. 31, 2022

(30) Foreign Application Priority Data

Jan. 29, 2019 (CH) .................................... 00096/19
Apr. 5, 2019 (CH) .................................... 00464/19

(51) Int. Cl.
*A61N 1/36* (2006.01)
*A61N 1/05* (2006.01)
*A61N 1/378* (2006.01)

(52) U.S. Cl.
CPC ....... *A61N 1/36007* (2013.01); *A61N 1/0521* (2013.01); *A61N 1/378* (2013.01)

(58) Field of Classification Search
CPC .. A61N 1/36007; A61N 1/0521; A61N 1/378; A61B 5/4381; A61B 5/205;
(Continued)

(56) References Cited

U.S. PATENT DOCUMENTS 4,742,833 A * 5/1988 Barsom .................. A61N 1/321
607/143
5,370,671 A * 12/1994 Maurer ................ A61N 1/0524
607/138
(Continued)

FOREIGN PATENT DOCUMENTS

CN 101175458 A 5/2008
JP H0852133 A 2/1996
(Continued)

OTHER PUBLICATIONS

Daniele Bianchi et al, "Correlation between penile cuff test and pressure-flow study in patients candidates for trans-urethral resection of prostate", BMC Urology, Biomed Central, Dec. 19, 2014, vol. 14, No. 1, p. 103, XP021207984.
(Continued)

*Primary Examiner* — Mallika D Fairchild
(74) *Attorney, Agent, or Firm* — CANTOR COLBURN LLP

(57) ABSTRACT

An urinary pumping device for generating a fluid flow through a urethra of a patient includes an activation arrangement configured to induce intermittent compression and release of the urethra, and a mounting structure to mount and unmount the activation arrangement to a body of the patient. The mounting structure is configured to position the activation arrangement on the body of the patient such that the urethra of the patient can be intermittently compressed and released by the activation arrangement.

20 Claims, 6 Drawing Sheets

(58) Field of Classification Search
CPC ...... A61B 5/208; A61F 2/0009; A61F 2/0031; A61F 2/0036; A61F 2/0045; A61F 2/005; A61F 2/0054
See application file for complete search history.

(56) References Cited

U.S. PATENT DOCUMENTS

| | | | | | |
|---|---|---|---|---|---|
| 5,571,118 | A * | 11/1996 | Boutos | A61H 19/30 | 607/143 |
| 5,807,278 | A * | 9/1998 | McRae | A61B 5/4381 | 600/573 |
| 6,128,536 | A * | 10/2000 | Noack | A61N 1/36007 | 607/39 |
| 2003/0018365 | A1* | 1/2003 | Loeb | A61N 1/36007 | 607/40 |
| 2004/0116773 | A1 | 6/2004 | Furness et al. | | |
| 2004/0129277 | A1 | 7/2004 | Parkes | | |
| 2005/0055063 | A1 | 3/2005 | Loeb et al. | | |
| 2009/0247817 | A1* | 10/2009 | Forsell | A61N 1/3605 | 607/113 |
| 2009/0306460 | A1 | 12/2009 | Stephens et al. | | |
| 2010/0168784 | A1* | 7/2010 | Pustilnik | A61B 50/31 | 606/193 |
| 2017/0014217 | A1 | 1/2017 | Patrusky | | |

FOREIGN PATENT DOCUMENTS

| | | | |
|---|---|---|---|
| JP | 2009247691 | A | 10/2009 |
| JP | 3198730 | U | 7/2015 |
| WO | 9955251 | A1 | 11/1999 |
| WO | 0110357 | A1 | 2/2001 |

OTHER PUBLICATIONS

International Search Report issued Apr. 8, 2020 re: Application No. PCT/EP2020/052115, pp. 1-6, citing: US 5 807 278 A, Daniele Bianchi et al. "Correlation between penile cuff test . . . ", US 2004/0129277 A1 and US 2004/0116773 A1.

Written Opinion issued Apr. 8, 2020 re: Application No. PCT/EP2020/052115, pp. 1-7, citing: US 5 807 278 A, Daniele Bianchi et al. "Correlation between penile cuff test . . . ", US 2004/0129277 A1 and US 2004/0116773 A1.

Chinese Office Action for Chinese Application No. 202080023543.9, dated Jul. 30, 2023, 9 pages, English translation.

Japanese Office Action for Japanese Application No. 2021-543267, dated Sep. 26, 2023, 7 pages, English translation.

* cited by examiner

URINARY PUMPING DEVICE

TECHNICAL FIELD

The present disclosure relates to a urinary pumping device according to the preamble of independent claim 1. Such devices can be used for generating a fluid flow through an urethra of a patient.

BACKGROUND

Today an increasing number of persons suffer from urological defects. Particularly, due to the increasing expectation of life in developed countries, urological dis-functions are getting more common. One kind of such urologic dis-functions relates to underactive bladders. Patients being confronted with an underactive bladder typically are not able completely empty the bladder such that a residual portion of urine stays inside the bladder even after naturally emptying the bladder.

Such residual urine in the bladder may cause discomfort to the patient since urge to empty the bladder stays. It may also cause inflammations or other secondary diseases.

For treating patients having an underactive bladder it is known to introduce a pipe or catheter through the urethra into the bladder in order to remove the residual urine from the bladder. However, even though such process allows for sufficiently emptying the bladder it is comparably delicate and complicated to apply. In particular, introducing the pipe often is undesired and requires the operator or patient to be trained for not affecting the patient. Furthermore, such emptying of the bladder makes it necessary that appropriate equipment, which may be comparable bulky and/or heavy, is accessible. Additionally, using catheters may cause urinary infections.

Therefore, there is a need for an improved, easily applicable system or device allowing emptying the bladder of a patient.

SUMMARY

According to the disclosure, this need is settled by a urinary pumping device as it is defined by the features of independent claim 1. Preferred embodiments are subject of the dependent claims.

In a first aspect, the disclosure is a urinary pumping device for generating a fluid flow through an urethra of a patient, comprising (i) an activation arrangement configured to induce intermittent compression and release of the urethra, and (ii) a mounting structure to mount and unmount the activation arrangement to a body of the patient. The mounting structure is configured to position the activation arrangement on the body of the patient such that the urethra of the patient is intermittently compressed and released by means of the activation arrangement.

By being capable of compressing and releasing the urethra, the device can operate as a peristaltic pump or as an impedance pump. Thereby, when being operated as a peristaltic pump the activation arrangement can be configured to compress and/or expand neighbouring sections of the urethra one after the other. Like this, the urine is pushed forward from the bladder into the urethra and outside through wave-like movements. When being operated as an impedance pump the activation arrangement can be configured to compress and/or expand the urethra at specific frequency and location. Vice versa, a liquid or fluid can be pumped into the bladder by operating the impedance pump in an opposite direction. Such filling of the bladder can be provided for therapeutic purposes. Also, an alternating filling and emptying of the bladder may be induced for therapeutic purposes.

The fluid to be pumped by the device can particularly be a liquid. More specifically, it can be urine to be pumped out of the bladder, a liquid medicament or another therapeutic liquid such as a saline solution to be pumped into the bladder.

The mounting and unmounting or demounting of the activation arrangement is a non-surgical or non-invasive operation. In particular, it is an operation performed from outside the body of the patient. Thereby, in some embodiments it can involve positioning something in a body cavity which is accessible from the outside such a vagina. However, any surgical or other invasive step is excluded from the mounting and unmounting in accordance with the disclosure. Thus mounting and unmounting the activation arrangement on the body can be mounting the activation arrangement at or in the body and unmounting it off or from the body. Typically, the mounting and unmounting of the activation arrangement can be done by the patient himself/herself such that it can be referred to as self-mounting or self-unmounting, respectively.

It is possible that the patient or another person manually mount and unmount the activation arrangement. For example, the activation arrangement may be manually pushed or positioned at an appropriate spot of the body of the patient at which the urethra is accessible. In such an application the mounting structure may be embodied at or in the activation arrangement in order to receive the hand or another body part of the patient or other person for pushing or positioning the activation arrangement at the spot of the body. Additionally or alternatively, in such embodiments the mounting structure may include a structure or shape at the activation arrangement which is configured to receive the spot of the body part. For example, this structure may be shaped to receive a penis of the patient.

In particular, in such a manually applicable embodiment of the urinary pumping device according to the disclosure, the mounting structure preferably comprises a penis accommodation section configured to accommodate the penis of the patient such that the urethra of the patient can be intermittently compressed and released by means of the activation arrangement when the penis of the patient is accommodated on the penis accommodation section.

For example, such manually applicable embodiment of the urinary pumping device may be realized as a handheld device which is manually applied to the patient. Thereby, the mounting structure preferably comprises a finger accommodation section configured to accommodate at least one finger of the patient when another finger of the patient pushes the penis of the patient to the penis accommodation section. For example, the finger accommodation section and the penis accommodation section are located at quasi opposite sides of the handheld device. This allows for a convenient and efficient pushing of the penis to the penis accommodation section.

Thereby, the activation arrangement preferably comprises a pushing member configured to press the penis of the patient when the penis of the patient is accommodated on the penis accommodation section.

The term "inducing intermittent compression and release of the urethra" in the context of the disclosure relates to a direct modification, i.e. compression and release, of the urethra as well as to an indirect modification. Direct modification can, e.g., be embodied by physically pressing the urethra or its neighbouring tissue. Indirect modification can, e.g., be embodied by activating a muscle such as the urethral sphincter which in turn compresses and releases the urethra.

The urinary pumping device according to the disclosure allows for providing a fluid out of or into the bladder. By being self-operatable the device allows for a convenient application. Like this, acceptance of a treatment can be increased such that the quality of the treatment can be improved.

For example, in one embodiment the urinary pumping device is comparably small such that it is easily portable. The patient then mounts the activation arrangement before urinating, operates the urinary pumping device during urinating such that the bladder is more or less completely emptied and then unmounts the activation arrangement after finishing urinating. Also, the patient can constantly wear the device or the activation arrangement thereof. In such application, a remote control can be particularly beneficial.

In a preferred embodiment, the activation arrangement comprises a surrounding portion dimensioned to be arranged around a penis of the patient. Such surrounding portion can, e.g., be designed to be pulled on the penis or to be wrapped around the penis. When being mounted, the surrounding portion can extend about the complete circumference of the penis or a portion thereof. Such surrounding portion allows for efficiently acting on the penile urethra and thereby inducing pumping, e.g. as a peristaltic or impedance pump. Like this, the urinary pumping device can efficiently be designed for male patients.

Thereby, the activation arrangement preferably comprises a diameter adjuster configured to reduce a diameter of the surrounding portion when being arranged around the penis of the patient. Such diameter adjuster allows for efficiently pressurizing the penile urethra and thereby inducing a pumping either from or towards the bladder.

Thereby, the surrounding portion of the activation arrangement preferably has a recess or gap interrupting the surrounding portion in its circumference and the diameter adjuster of the activation arrangement is configured to change the circumferential extension of the recess or gap. By changing the extension or dimension of the recess or gap, the diameter of the surrounding portion can be varied. For example, when reducing the circumferential extension of the recess the diameter of the surrounding portion is reduced correspondingly. Like this, the penile urethra can efficiently be pressurized.

Preferably, the diameter adjuster of the activation arrangement comprises a lever pivotably mounted to the surrounding portion at one side of the recess and connected to the other side of the recess. The term "pivotably" in this context can relate to a rotation about a specific angle or to a complete or 360° rotation. The lever can be connected to the other side of the recess by means of a band, cable, rod or any other suitable structure. By such pivotable lever the diameter of the surrounding portion can efficiently be varied. In particular, it can be varied in repetitive cycles such that intermittent compression and release of the penile urethra can efficiently be implemented.

Thereby, the diameter adjuster of the activation arrangement preferably comprises a drive coupled to the lever and configured to pivot the lever. Such drive can, e.g., have an electro-motor, a linear motor or the like. It allows for precisely and efficiently adjusting the diameter of the surrounding portion.

The surrounding portion can be or comprise a cuff or cuff-like structure configured to be wrapped around the penis. Preferably, the surrounding portion is embodied as or comprises a ring portion. In this context, the term "ring portion" covers sections of rings as well as complete or closed rings. Typically, the ring portion is designed to extend over a major part of the circumference of the penis. Such a ring portion or ring can efficiently be pulled or arranged over or on the penis such that a convenient application is possible.

Particularly in embodiments where the fluid is to be peristaltically pumped, the activation arrangement can comprise plural surrounding portions such as plural rings or a series of rings, or the surrounding portion can be equipped with plural sections individually being variable in diameter.

In one variant, the surrounding portion of the activation arrangement preferably comprises a dimension variable material which exhibits a change of a diameter of the surrounding portion when stimulated. Stimulation can be induced by any suitable and feasible means such as by temperature variation, radiation, pressure induction or the like. Such dimension variable material can allow for efficiently reducing the diameter of the surrounding portion and, thereby, pressurizing the penile urethra. Thereby, the dimension variable material of the surrounding portion of the activation arrangement preferably is a polymeric material.

In another variant, the activation arrangement preferably comprises a pushing member mounted to the surrounding portion, wherein the pushing member is configured to press the penis of the patient. The pushing member can be any suitable structure such as a rod, a sphere, a cylinder, a hammer or the like. Such pushing member allows for selectively pressurizing the penis at a location where the urethra can be reached. Thereby, the urinary pumping device preferably comprises a drive coupled to the pushing member and configured to tilt the pushing member. Such drive allows for efficiently pressurizing the penile urethra. Alternatively, the urinary pumping device can comprise a drive coupled to the pushing member which is configured to linearly move the pushing member back and forth. For example, the drive can have a linear motor which induces a translational movement to pushing member.

In another preferred embodiment, the activation arrangement comprises a plug portion dimensioned to be arranged in the vagina of the patient. When being mounted, such plug portion allows for efficiently acting on the urethra neighbouring the vagina and thereby inducing pumping, e.g., as a peristaltic or impedance pump. Like this, the urinary pumping device can efficiently be designed for female patients.

In one variant, the activation portion preferably comprises a plug adjuster configured to vary a diameter of the plug portion when being arranged in the vagina of the patient. Since the diameter of the plug portion typically is correlated or representing a thickness of the plug portion, by varying the diameter, a pressure can be applied to and released from the urethra via a wall of the vagina.

Preferably, the plug portion of the activation arrangement comprises a dimension variable material which exhibits a change of a diameter of the plug portion when stimulated. Thereby, the dimension variable material of the plug portion of the activation arrangement preferably is a polymeric material. Such embodiment of the plug portion allows for an efficient activation or operation.

In another variant, the plug portion preferably comprises a pushing section configured to press the vagina of the patient towards the urethra. The pushing section can be any suitable structure such as a rod, a sphere, a cylinder, a hammer or the like. Thereby, the urinary pumping device preferably comprises a drive coupled to the pushing section of the plug portion and configured to tilt the pushing section.

Like this, the urethra can efficiently be pushed or pressurized such that pumping can be induced.

In still another preferred embodiment, the activation arrangement preferably comprises electrode elements configured to be arranged at the body of the patient such that the urethral sphincter of the patient is stimulatable by an electric field generated by the electrode elements of the activation arrangement. Stimulation of the urethral sphincter can particularly cause a contraction of the urethral sphincter. The electrode elements can comprise a coil or a similar structure. The electrode elements can be embodied or applied to directly stimulate the urethral sphincter or to indirectly stimulate the urethral sphincter via a nerve or the like.

For female patients, preferably the plug portion of the activation arrangement embodies at least one of the electrode elements of the activation arrangement. This allows for an efficient embodiment of the electrode element which can conveniently be positioned at an appropriate location where the urethra or urethral sphincter is accessible.

Preferably, the urinary pumping device comprises a control unit configured to control the activation arrangement such that a periodic compression and release of the urethra is generated by the activation arrangement at a predefined frequency and, optionally, a predefined amplitude, a predefined pressure, a predefined force and/or a predefined duty cycle. Such control unit allows for efficiently manipulate the device such that it can be adjusted to the given situation and/or needs of the patient. Further, by predefining the frequency an impedance pumping can be induced.

Thereby, the predefined preferably frequency is in a range of about 1 Hz to about 50 Hz and, preferably, in a range of about 5 Hz to about 20 Hz. Such frequency can be appropriate to induce a flow of urine from the bladder to outside the body by means of impedance pumping. Like this, the more or less complete content of the bladder can be delivered outside the body such that quasi no urine resides in the bladder. Advantageously, the frequency is not constant over time but adapted as function of the flow or of the bladder volume. Such adaptation can be provided manually or automatically by the control unit.

Preferably, the urinary pumping device comprises a power supply unit configured to provide power to the activation arrangement. The power supply unit can be integral with the other components of the device. For example, the activation arrangement, mounting structure and power supply unit can be arranged in one piece and, e.g., arranged in a housing. Preferably, the power supply unit is separate from the activation arrangement and the mounting structure such that it is positionable remote from the activation arrangement and the mounting structure. The power supply can, thus, be arranged distant from the mounting structure such that the mounting structure can be embodied comparably compact. Like this, the elements to be positioned at a location of the body at which the urethra is accessible, such as the penis, can be less bulky and less heavy. Like this patient's comfort when using the urinary pumping device can be increased such that also acceptance of the device can be increased.

Preferably, the urinary pumping device comprises a control unit configured to adjust the activation arrangement. The control unit can be integral with the other components of the device or in a separate physical entity. When being a separate entity, the control unit can be connected to the activation arrangement or other components of the device by a wire or wirelessly. For a wireless communication the device can be equipped with a wireless communication adapter at the control unit entity and a corresponding wireless communication adapter at the entity comprising the activation arrangement. Particularly a wireless connected control unit can be beneficial in operating the device.

In a second aspect, the disclosure relates to a use of electrode elements to generate a fluid flow through an urethra. The use comprises attaching the electrode elements to a body of the patient such that a urethral sphincter of the patient is within an electric field generatable by the electrode elements; and intermittently activating the electrode elements such that the electric field is intermittently generated and the urethral sphincter is intermittently stimulated. Like this, a convenient and efficient pumping of fluid can be achieved.

To achieve at least some of the effects and benefits of the urinary pumping device according to the disclosure and its preferred embodiments described above, as alternatives to the urinary pumping device according to the disclosure the following urinary pumping devices can be provided.

In a third aspect, the disclosure is a urinary pumping device for generating a fluid flow through an urethra of a patient, comprising an activation arrangement configured to induce intermittent compression and release of the urethra, and a positioning unit, wherein the activation arrangement is mounted to the positioning unit and the positioning unit is arranged such that a body of the patient is locatable by the patient relative to the activation arrangement such that the urethra of the patient is accessible to the activation arrangement such that it is intermittently compressible and releasable by means of the activation arrangement.

The positioning unit of the urinary pumping device of the third aspect of the disclosure can be or be implemented in a good or device of daily use of the patient. Preferably, the positioning unit comprises a toilet or toilet seat which is equipped with the activation arrangement. Thereby, the toilet or toilet seat can be any standard toilet or toilet seat to which the activation arrangement is mounted or fixed to. For equipping the toilet or toilet seat with the activation arrangement, an auxiliary structure such as a band or strap, a fixed mounting such as a rigid part to be plugged to the toilet or a similar construction can be used. Alternatively, the positioning unit can be or comprise a piece of clothes such as a pair of underpants, a bed such as a hospital bed, a bathtub, or the like.

Particularly when the positioning device is embodied comprising a toilet or toilet seat but also in other configurations, the urinary pumping device of the third aspect of the disclosure can operate in a similar manner as the urinary pumping device of the first aspect of the disclosure. Thereby, it can be particularly comfortable in use, since it is not required to mount any structure or part to the body of patient. Rather, the activation arrangement can be appropriately positioned to access the urethra of the patient only when being located on or at the positioning unit. For example, if the positioning unit is a toilet or toilet seat, the location and orientation of the patient is more or less predefined when sitting on the toilet or toilet seat. Thus, the activation arrangement can be mounted precisely enough for being capable of accessing the urethra when the patient uses the toilet.

The following embodiments of urinary pumping devices of the third aspect of the disclosure allow to achieve the effects and benefits described above in connection with the respective preferred embodiments of the urinary pumping device according to the first aspect of the disclosure.

Preferably, the activation arrangement of the third aspect of the disclosure comprises a pushing member mounted and configured to press the body of the patient at an appropriate location to compress the urethra of the patient.

Preferably, the urinary pumping device of the third aspect of the disclosure comprises a drive coupled to the pushing member and configured to move the pushing member to compress the urethra of the patient.

Preferably, the activation arrangement of the third aspect of the disclosure comprises electrode elements mounted and configured to be arranged at the body of the patient such that the urethral sphincter of the patient is stimulatable by an electric field generated by the electrode elements of the activation arrangement.

Preferably, the urinary pumping device of the third aspect of the disclosure comprises a control unit configured to control the activation arrangement such that a periodic compression and release of the urethra is generated by the activation arrangement at a predefined frequency and, optionally, a predefined amplitude, a predefined pressure, a predefined force and/or a predefined duty cycle.

Preferably, this predefined frequency is in a range of about 1 Hz to about 50 Hz and, preferably, in a range of about 5 Hz to about 20 Hz.

Preferably, the urinary pumping device of the third aspect of the disclosure comprises a power supply unit configured to provide power to the activation arrangement.

Preferably, the urinary pumping device of the third aspect of the disclosure comprises a control unit configured to adjust the activation arrangement.

Furthermore, at least some of the effects and benefits of the urinary pumping device according to the disclosure and its preferred embodiments described above can also be achieved by manual operation. Therefore, a method of generating a fluid flow through an urethra of a patient may comprise the following steps: localizing a spot on the body of the patient at which the urethra is accessible; positioning a finger or another body part at the localized spot; and the finger or body part intermittently pushing and releasing the localized spot. The finger or body part can be of the patient itself or of another person.

BRIEF DESCRIPTION OF THE DRAWINGS

The urinary pumping device according to the disclosure is described in more detail herein below by way of exemplary embodiments and with reference to the attached schematic drawings, in which.

DETAILED DESCRIPTION OF THE DRAWINGS

In the following description certain terms are used for reasons of convenience and are not intended to limit the disclosure. The terms “right”, “left”, “up”, “down”, “under” and “above” refer to directions in the figures. The terminology comprises the explicitly mentioned terms as well as their derivations and terms with a similar meaning. Also, spatially relative terms, such as “beneath”, “below”, “lower”, “above”, “upper”, “proximal”, “distal”, and the like, may be used to describe one element’s or feature’s relationship to another element or feature as illustrated in the figures. These spatially relative terms are intended to encompass different positions and orientations of the devices in use or operation in addition to the position and orientation shown in the figures. For example, if a device in the figures is turned over, elements described as “below” or “beneath” other elements or features would then be “above” or “over” the other elements or features. Thus, the exemplary term “below” can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
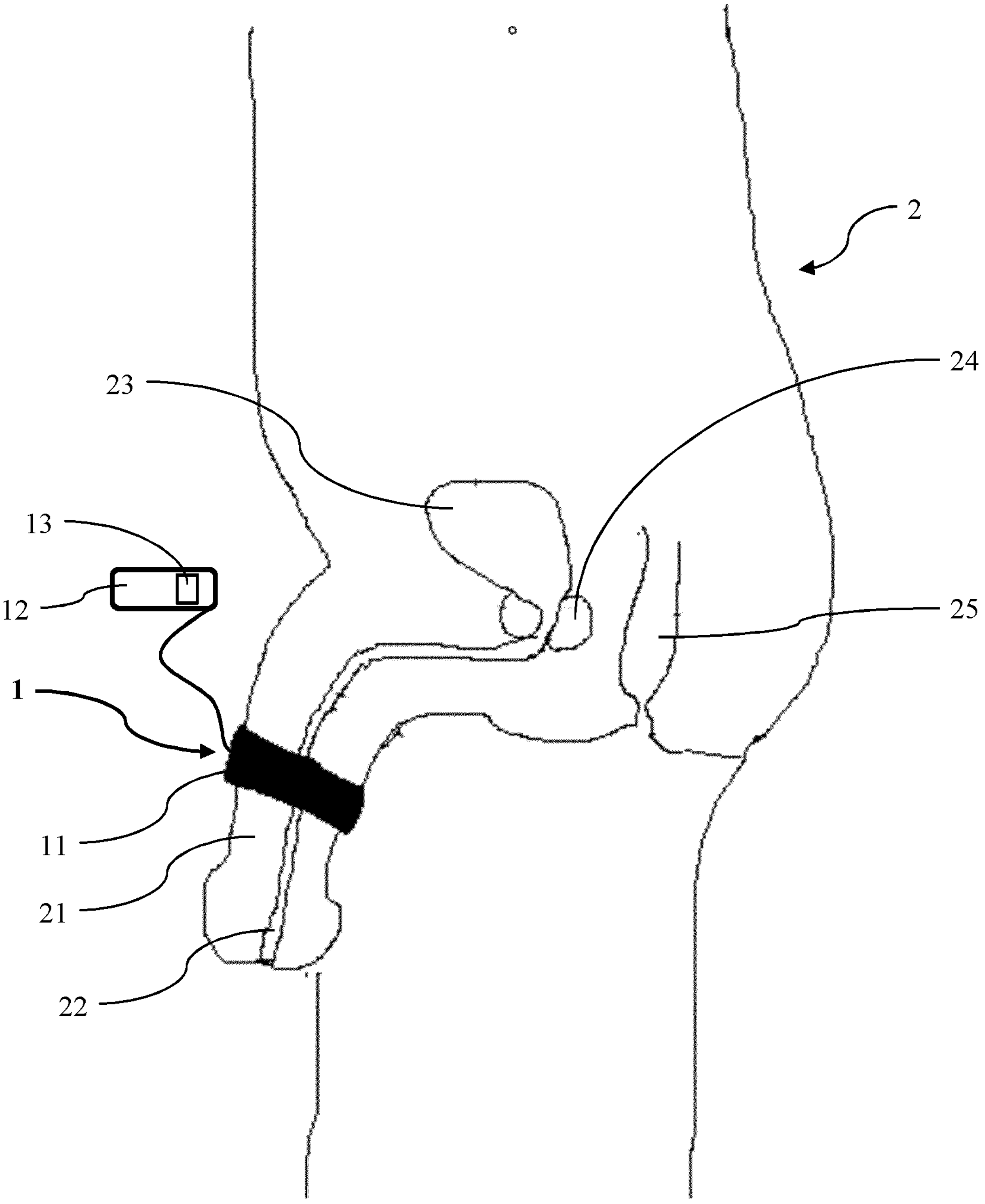
FIG. 1 shows a schematic view of a first embodiment of a urinary pumping device according to the disclosure for a male patient.

FIG. 1 shows a first embodiment of a urinary pumping device 1 applied to a male patient 2. The male patient 2 is schematically depicted such that some portions of inside his body are visible. In particular, a rectum 25, a bladder 23, a penis 21, an urethra 22 extending from the bladder 23 to an outlet of the penis 21, and a prostate 24 of the patient 2 are visible.

The urinary pumping device 1 comprises a cuff 11 wrapped around the penis 21 of the patient 2 as mounting structure and as surrounding portion of an activation arrangement, and a control unit 12 connected to the cuff 11 via a wire. Alternatively, the control unit 12 and the cuff 11 can also be equipped with adapters for wireless communication. I.e. the control unit 12 can be equipped with a sender and the cuff 11 with a corresponding receiver. The cuff 11 can conveniently be wrapped around and unwrapped from the penis 21 by the patient himself. The control unit 12 is equipped with a battery 13 as power supply unit. The cuff 11 is made of a dimension variable material which can be stimulated. Like this, the control unit 12 can exhibit a change of a diameter of the cuff 11 by stimulation.

The control unit 12 is configured to control the cuff 11 such that a periodic compression and release of the urethra 22 is generated by the cuff 11. More specifically, the control unit 12 induces the periodic compression and release of the urethra at a frequency in a range of about 5 Hz to about 20 Hz, at a predefined amplitude, a predefined duty cycle, a predefined force and a predefined pressure. These parameters can be adjusted by the patient 2 via the control unit 12. In this way, an impedance pump is implemented in the urethra 22 such that a flow of urine is induced from the bladder 23 to outside the patient's 2 body. In this way, the bladder 23 can be more or less completely emptied such that quasi no urine resides in the bladder 23.

Figure 2:
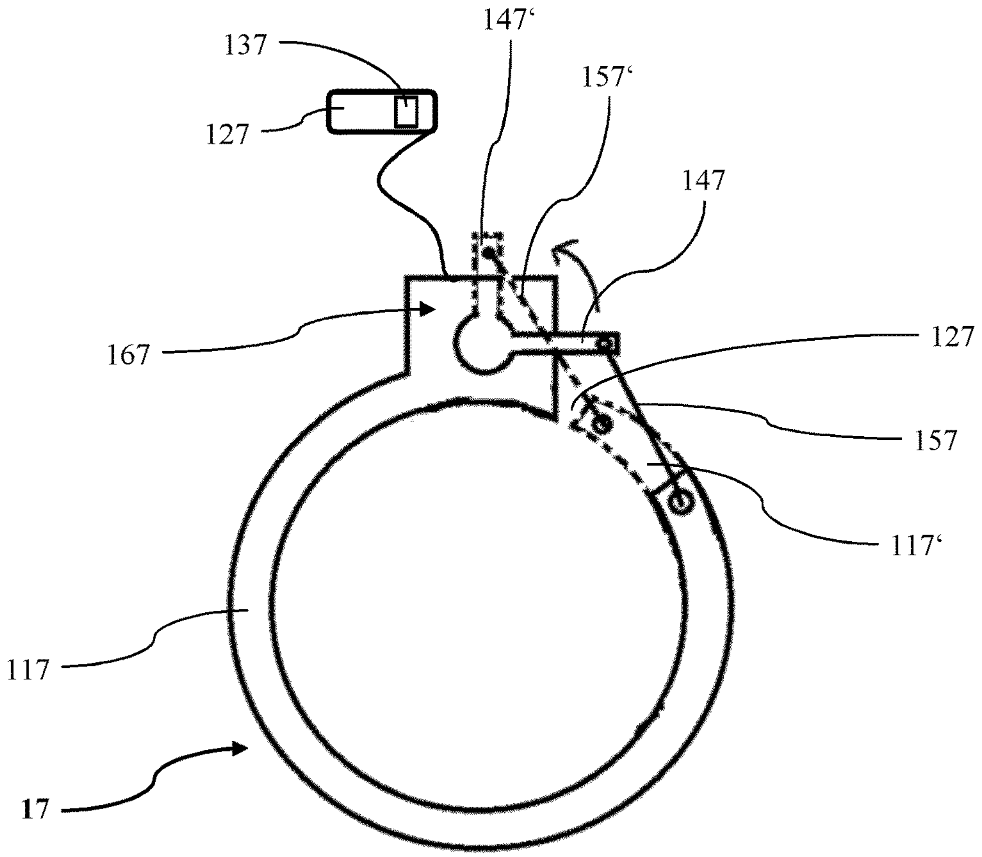
FIG. 2 shows a schematic view of a second embodiment of a urinary pumping device according to the disclosure for a male patient.

In FIG. 2 a second embodiment of a urinary pumping device 17 is shown. It comprises a control unit 127 with a battery 137 as power supply unit, and a ring portion 117 as mounting structure and as surrounding portion of an activation arrangement. The ring portion 117 is connected to the control unit 127 via a wire. It can conveniently be positioned on and removed from the penis of a patient. A recess 127 interrupts the ring portion 117 in its circumference such that it does not form a closed but an open ring. At one side of the recess 127 the ring portion houses a drive coupled to a lever 147. In particular, the lever 147 is coupled to the drive and mounted to the ring portion 117 at one of its longitudinal ends such that it can be pivoted or tilted by the drive. The other longitudinal end of the lever 147 is connected to the ring portion 117 at the other side of the recess 127 by means of a cable 157. The cable 157, the lever 147 and the drive are comprised by a diameter adjuster 167 of an activation arrangement.

The diameter adjuster 167 is configured to change the circumferential extension of the recess 127. More specifically, by tilting the lever 147 from a horizontal position about 90° to a vertical position, the cable 157 pulls the other side of the ring portion 117. The ring portion 117 is made of an elastic material which allows an elastic deformation. In the end, the vertical lever 147' pulls the ring portion 117' at the other side of the recess 127 via the cable 157' such that the circumferential extension of the recess 127 and, thereby, a diameter of the ring portion 117' are reduced. Thus, by pivoting or tilting the lever 147 back and forth the diameter of the ring portion 117 can be periodically reduced and enlarged.

In use, the ring portion 117 is arranged around a penis of a male patient and the urinary pumping device 17 is similarly operated as the urinary pumping device 1 described above in connection with FIG. 1. In particular, by periodically changing the diameter of the ring portion 117 when arranged around the penis, a periodic compression and release of a urethra of the patient is generated. Like this, urine can be pumped out of a bladder of the patient by way of impedance pumping.

Figure 3:
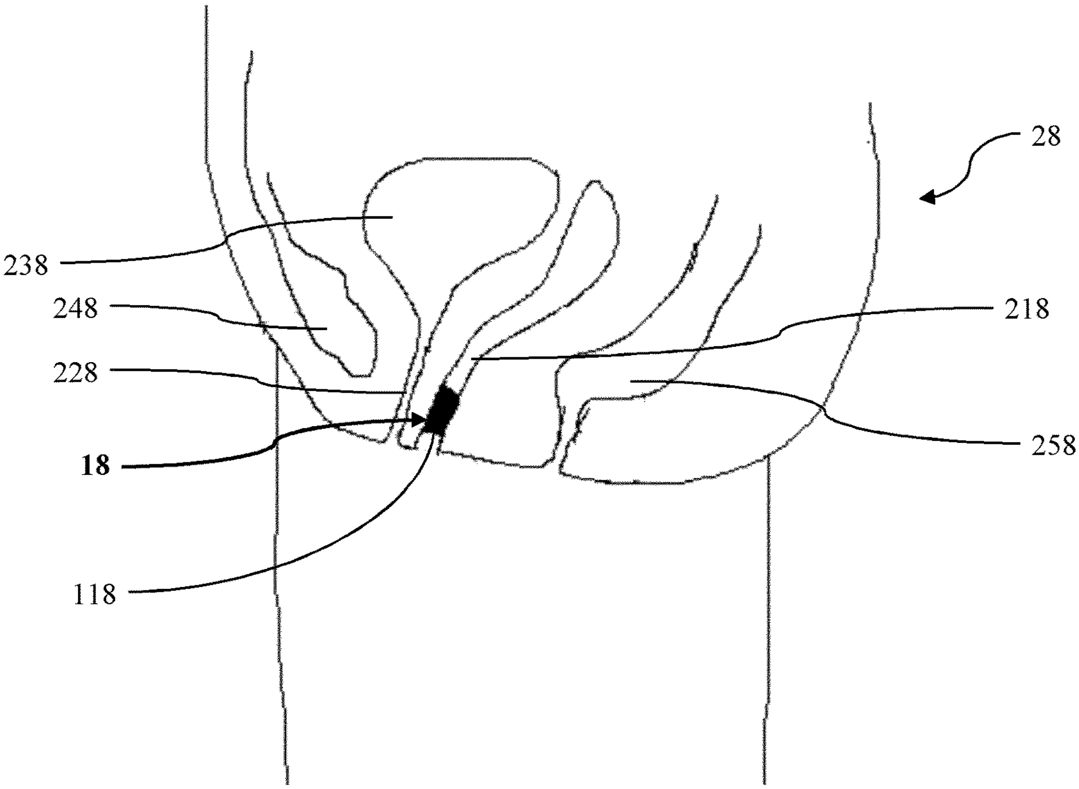
FIG. 3 shows a schematic view of a third embodiment of a urinary pumping device according to the disclosure for a female patient.

FIG. 3 shows a third embodiment of a urinary pumping device 18 applied to a female patient 28. The female patient 2 is again schematically depicted such that some portions of inside her body are visible. In particular, a rectum 258, a bladder 238, a vagina 218, an urethra 228 extending from the bladder 238 to an outlet and a pubic bone 248 of the patient 28 are visible.

Figure 4:
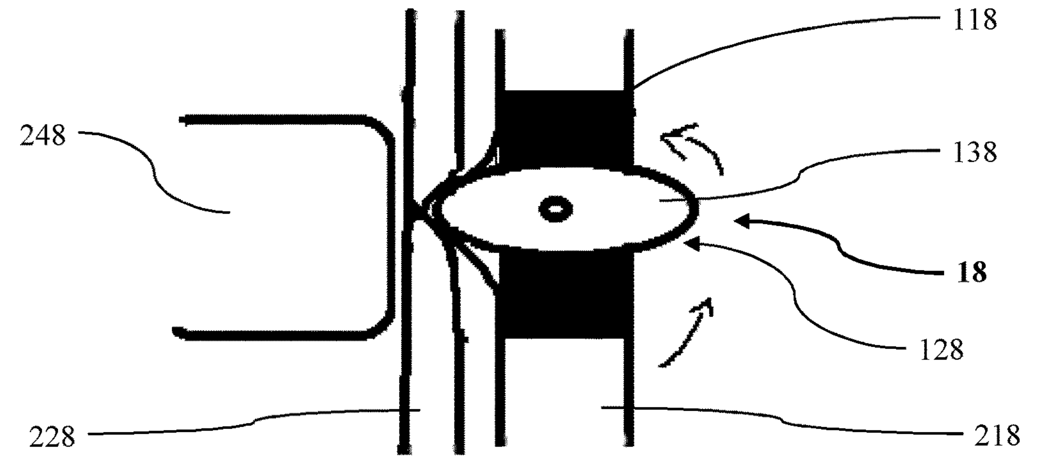
FIG. 4 shows a schematic detailed view on the urinary pumping device of FIG. 3.

The urinary pumping device 18 comprises a plug portion 118 as mounting structure introduced into the vagina 218 of the patient 28. The patient can conveniently introduce and remove the plug portion 118 to and from the vagina 218. As can be seen in FIG. 4, the urinary pumping device 18 has an activation portion with a plug adjuster 128 configured to vary a diameter or thickness of the plug portion 118 arranged in the vagina 218 of the patient 28. In particular, the plug adjuster 128 has an egg-shaped lever 138 pivotably or rotatably mounted to the plug portion 118. When being in a horizontal orientation while being rotated, the lever 138 forms a pushing section which presses the vagina 218 of the patient 28 towards her urethra 228. Thereby, the urethra 228 is compressed between the lever 138 and the pubic bone 248.

The urinary pumping device further comprises a drive coupled to the lever 138. The lever 138 is rotated at a speed such that a periodic compression and release of the urethra 228 is generated. Like this, an impedance pump is implemented in the urethra 228 such that a flow of urine is induced from the bladder 238 to outside the patient's 28 body.

Figure 5:
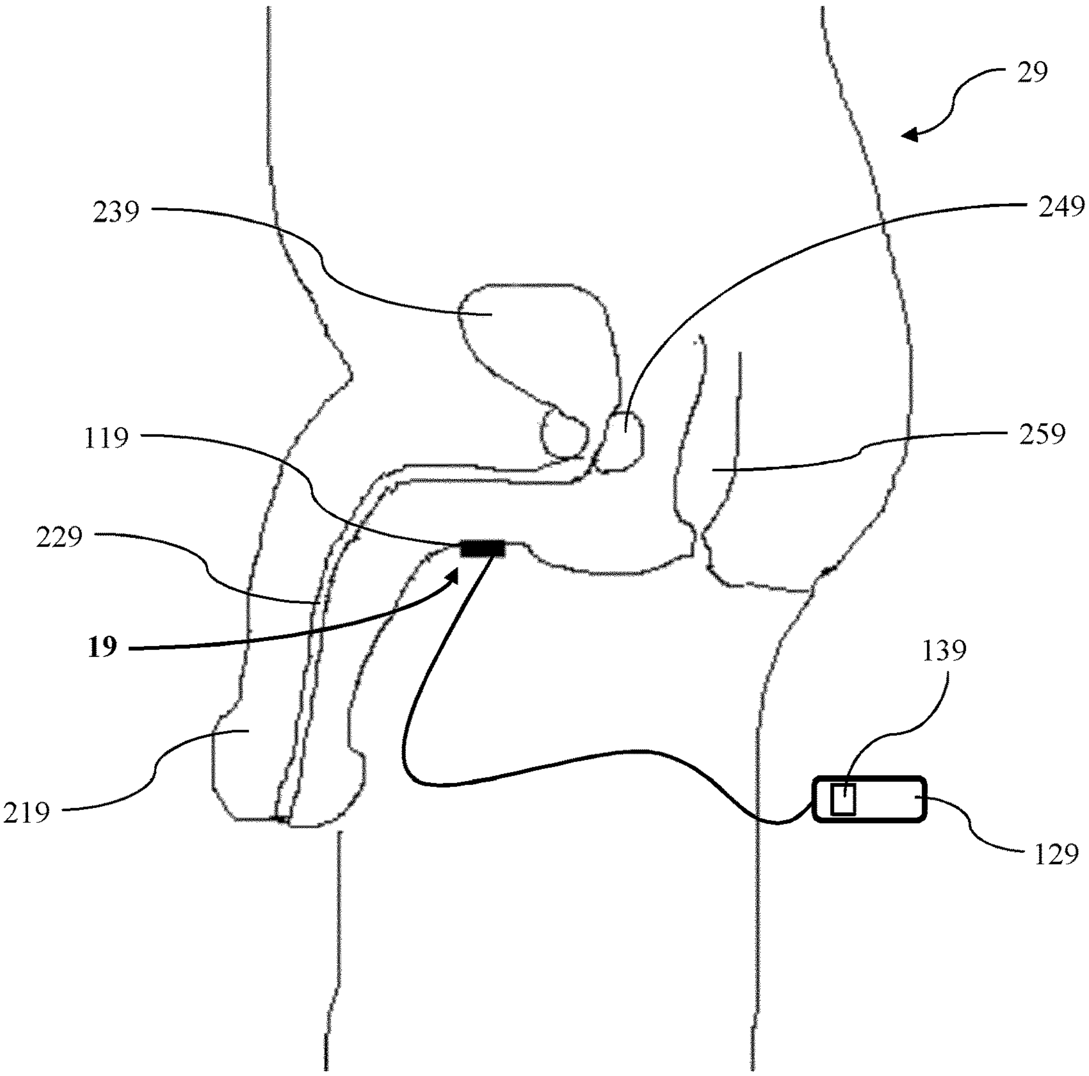
FIG. 5 shows schematic view of a fourth embodiment of a urinary pumping device according to the disclosure.

In FIG. 5 a fourth embodiment of a urinary pumping device 19 according to the disclosure is shown. The urinary pumping device 19 has an activation arrangement with electrode elements 119. The electrode elements 119 are provided with a mounting structure, such as an adhesive, to hold and arrange the electrode elements at the body of a male patient 29. The mounting structure allows the patient 29 to conveniently arrange and remove the electrode elements at and from the body of the patient 29. The male patient 29 is schematically depicted in FIG. 5 such that some portions of inside his body are visible. In particular, a rectum 259, a bladder 239, a penis 219, an urethra 229 extending from the bladder 239 to an outlet of the penis 219, and a prostate 249 of the patient 29 are visible.

The electrode elements 119 are connected via a wire to a control unit 129 which is equipped with a battery 139 as power supply unit. The control unit 129 is configured to operate the electrode elements 119 to generate an electric field. Thereby, the electrode elements 119 are positioned at the body such that an urethral sphincter of the patient 29 is stimulatable by the electric field generated by the electrode elements 119. More specifically, stimulation of the urethral sphincter causes a contraction of the urethral sphincter such that the urethra 229 is compressed. Like this, the control unit 129 can indirectly induce a periodic compression and release of the urethra 229 via the urethral sphincter. Thereby, a flow of urine is induced from the bladder 239 to outside the patient's 29 body.

Figure 6:
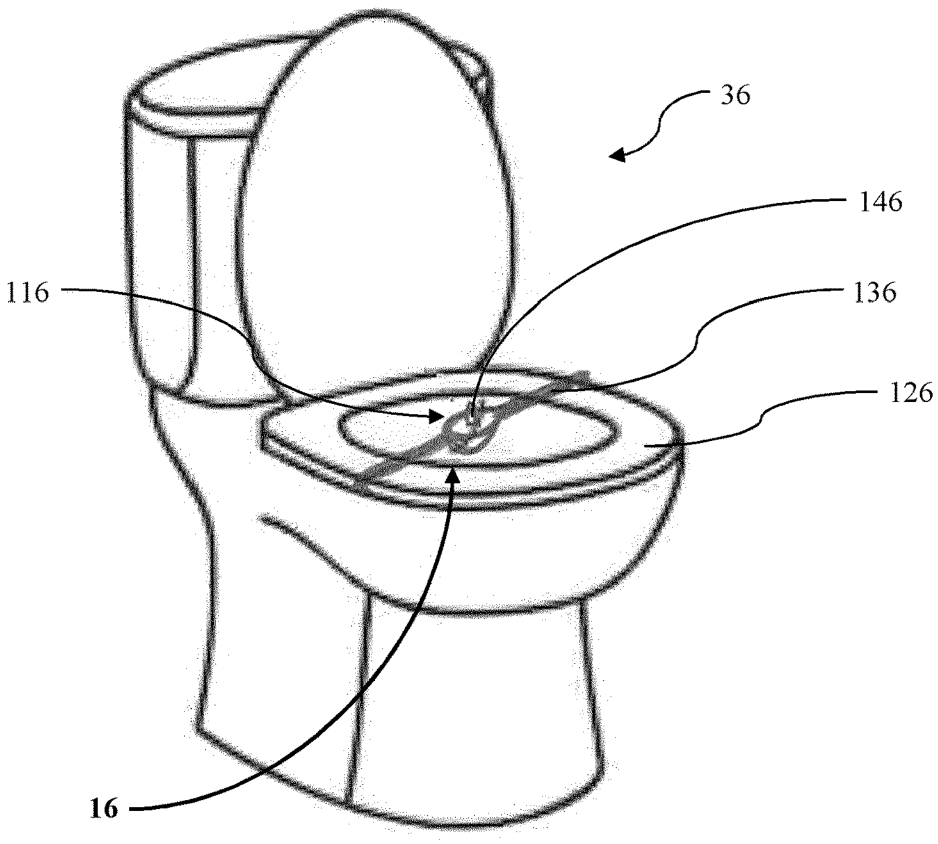
FIG. 6 shows a schematic perspective view of a fifth embodiment of a urinary pumping device according to the disclosure.

FIG. 6 shows a fifth embodiment of a urinary pumping device 16 according to the disclosure involving a toilet 36. The urinary pumping device 16 comprises an activation arrangement 116 and a positioning unit which has a strap 136 and a toilet seat 126. The activation arrangement 116 is mounted to the toilet 36 by means of the strap 136 which is fixed to the toilet seat 126. Thereby, the toilet seat 126 is conventionally mounted to a toilet bowl of the toilet 36.

Figure 7:
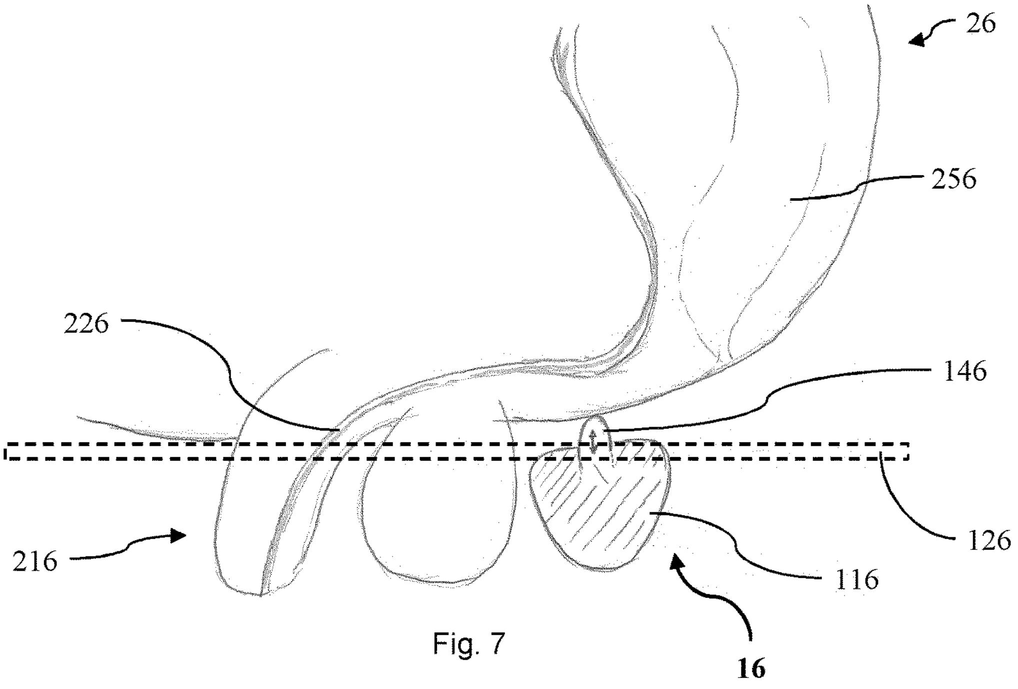
FIG. 7 shows a schematic side view of the urinary pumping device of FIG. 6 in operation.

As can be seen in FIG. 7, the toilet seat 126 and the strap 136 are arranged such that a body of a patient 26 is located in an appropriate position relative to the activation arrangement 116 when sitting on the toilet 36. In FIG. 7, an anus 256, a penis 216 and an urethra 226 of the patient are 26 exemplarily depicted. In the mentioned appropriate position, the urethra 226 of the patient 26 is accessible to the activation arrangement 116 such that a pushing member 146 of the activation arrangement 116 intermittently compresses and releases the urethra 226 when being operated.

For achieving such compression, the activation arrangement 116 is equipped with a pincher 146. In operation of the activation arrangement 116, the pincher 146 moves up and down such that the body of the patient 26 is pushed and released.

Figure 8:
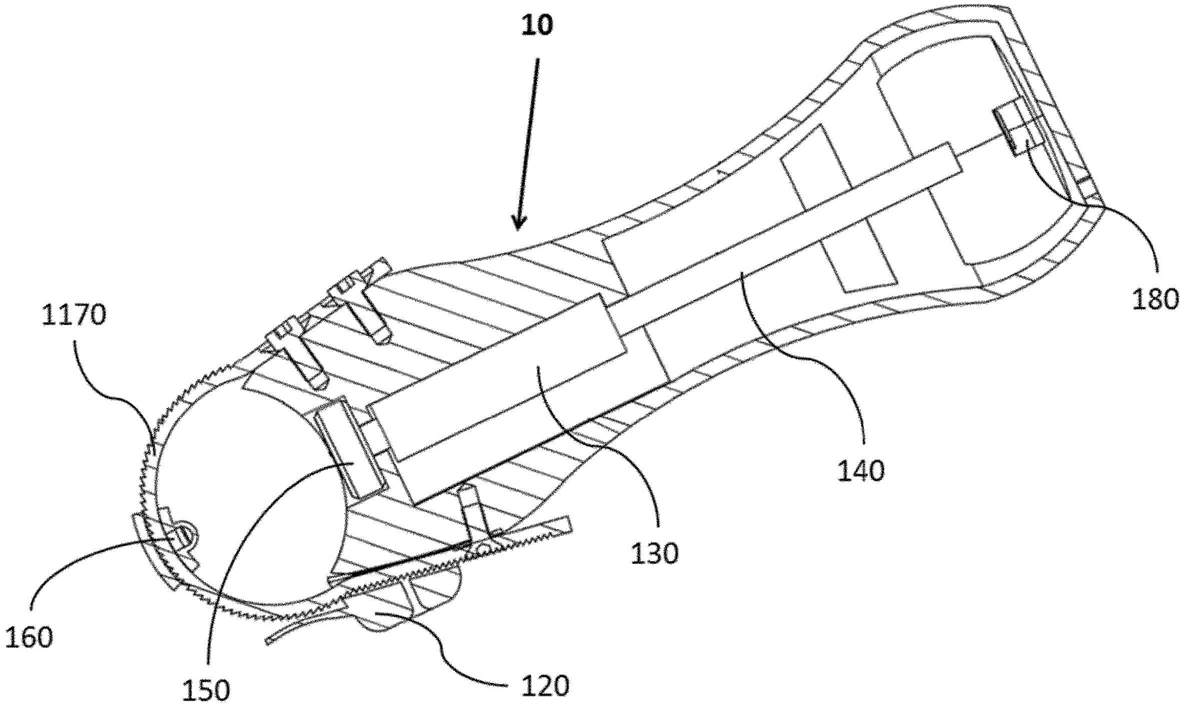
FIG. 8 shows a cross-sectional view of a sixth embodiment of a urinary pumping device according to the disclosure.

FIG. 8 shows a sixth embodiment of a urinary pumping device 10 according to the disclosure. The urinary pumping device 10 comprises a diameter adjuster and a ring portion 1170 as mounting structure and as surrounding portion of an activation arrangement. The ring portion 1170 is configured as a toothed belt which is pushed inside a ratchet 120 of the diameter adjuster. The ring portion 1170 can conveniently be positioned on and removed from a penis of a patient. The urinary pumping device 10 further comprises a shaft 140 and an electric motor 130, such as a linear motor, mounted internally of the urinary pumping device 10 as its drive. The electric motor 130 controls the motion of the shaft 140. A tip 150 of the diameter adjuster is mounted on the terminal part of the shaft 140 such that, when the shaft 140 is activated, the tip 150 compresses or releases the penis/urethra. Furthermore, a counter-tip 160 is mounted on the ring portion 1170, in the opposite position of the tip 150 to reach maximum compressing force in two points of the penis when the shaft 140 moves. The electric motor 130 is activated by the patient using a button 170 provided at a proximal end of the urinary pumping device 10. The button 170 can also be used to adjust the frequency, speed and force of the shaft 140.

Figure 9:
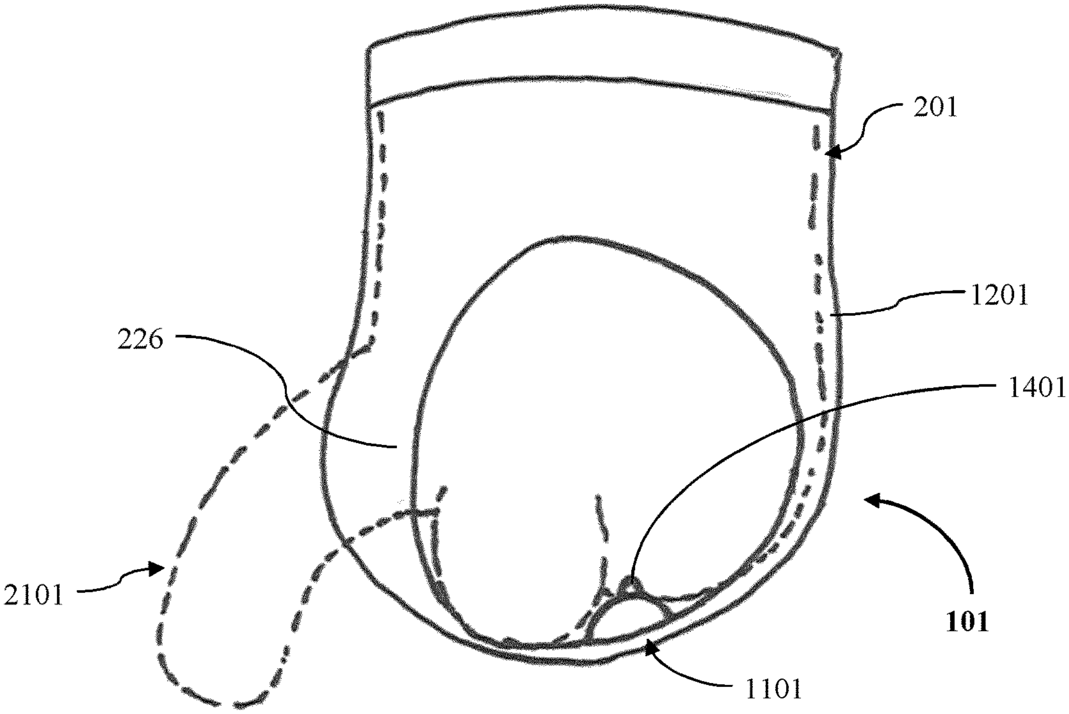
FIG. 9 shows a schematic side view of a seventh embodiment of a urinary pumping device according to the disclosure.

In FIG. 9 a seventh embodiment of a urinary pumping device 101 according to is shown. The urinary pumping device 101 comprises an activation arrangement 1101 and a positioning unit comprising a pair of underpants 1201. The activation arrangement 1101 is mounted to the underpants 1201 such that a body of a patient 201 is located in an appropriate position relative to the activation arrangement 1101 when wearing the underpants 201. The underpants 201 is equipped with a closable opening through which a penis 2101 of the patient 201 may be positioned when required for urinating. In the mentioned appropriate position, a urethra of the patient 201 is accessible to the an activation arrangement 116 such that a pushing member 1401 of the activation arrangement 116 intermittently compresses and releases the urethra 226 when being operated.

Figure 10:
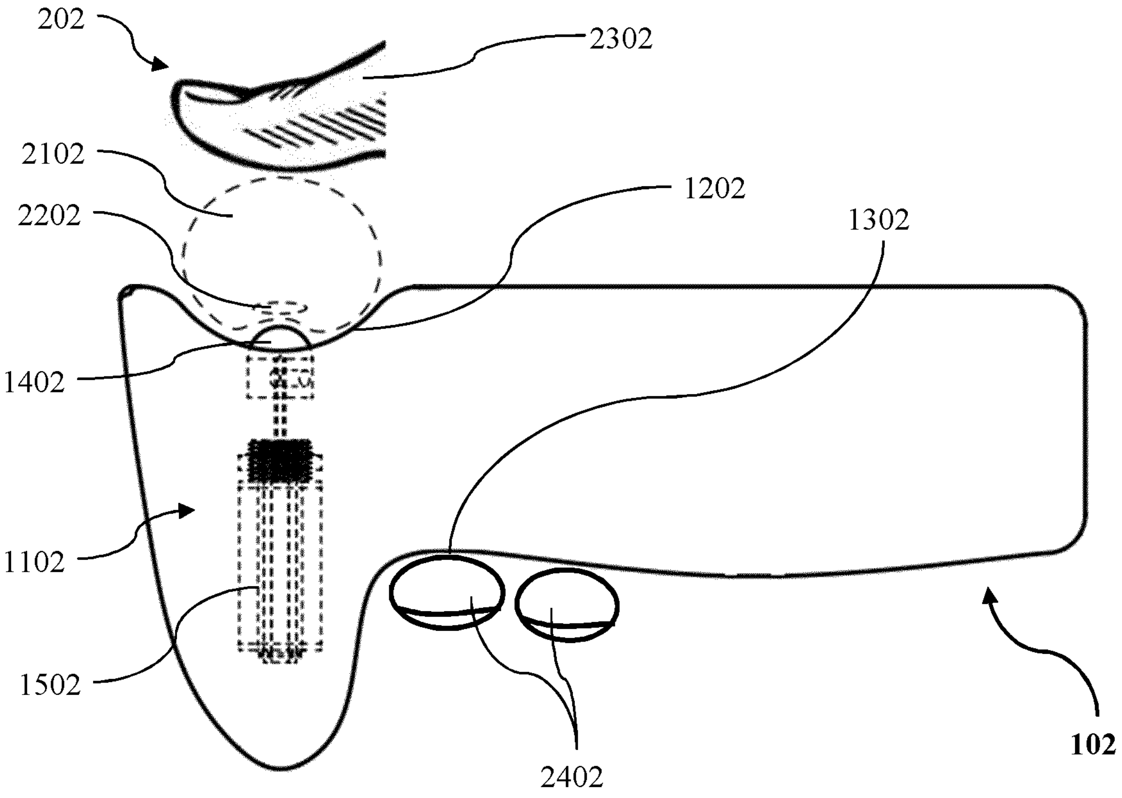
FIG. 10 shows a schematic side view of an eight embodiment of a urinary pumping device according to the disclosure.

FIG. 10 shows an eight embodiment of a urinary pumping device according to the disclosure realized as handheld apparatus 102. The handheld apparatus 102 comprises an elongated body, an activation arrangement 1102 and a positioning unit. The positioning unit is formed by a penis accommodating section 1202 at an upper side of the elongated body and a finger accommodating section 1302 at a lower side of the elongated body. The activation arrangement 1102 comprises a drive 1502 and a hemispherical pushing member 1402. The drive 1502 is arranged inside the body and the pushing member 1402 extends out of the body at the penis accommodation section 1202. The pushing member 1402 is coupled to the drive 1502 via a pole such that the drive 1402 can move the pushing member 1402 vertically up and down.

In use of the handheld apparatus 102, a patient 202 arranges his penis 2102 onto the penis accommodation section 1202 such that penile portion of a urethra 2202 is located adjacent to the pushing member 1402. The body of the handheld apparatus 102 is held in a hand of the patient 202 such that a thumb 2302 of one hand of the patient 202 is positioned on the penis 2102 and fingers 2402 of the same hand are positioned at the finger accommodating section 1302 of the body of the handheld apparatus 102. Like this, the handheld apparatus 102 is held and at the same time the penis is securely mounted at an appropriate location of the handheld apparatus 102. By the drive 1502 moving the pushing member 1402, the activation arrangement 1102 intermittently compresses and releases the urethra 2202 when being activated.

This description and the accompanying drawings that illustrate aspects and embodiments of the present disclosure should not be taken as limiting-the claims defining the protected disclosure. In other words, while the disclosure has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the disclosure. Thus, it will be understood that changes and modifications may be made by those of ordinary skill within the scope and spirit of the following claims. In particular, the present disclosure covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the disclosure or from disclosed subject matter. The disclosure comprises subject matter comprising the features defined in the claims or the exemplary embodiments as well as subject matter comprising said features.

Furthermore, in the claims the word “comprising” does not exclude other elements or steps, and the indefinite article “a” or “an” does not exclude a plurality. A single unit or step may fulfil the functions of several features recited in the claims. The mere fact that certain measures are recited in mutually different dependent claims does not indicate that a combination of these measures cannot be used to advantage. The terms “essentially”, “about”, “approximately” and the like in connection with an attribute or a value particularly also define exactly the attribute or exactly the value, respectively. The term “about” in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A urinary pumping device for generating a fluid flow through an urethra of a patient, the urinary pumping device comprising: a toilet seat equipped with an activation arrangement that comprises a pushing member and a drive coupled to the pushing member, said pushing member being configured to induce direct intermittent compression and release of the urethra by physically pressing urethra’s neighbouring tissue, wherein the activation arrangement is mounted to the toilet seat such that, when the patient is sitting on the toilet seat, the urethra of the patient is accessible to the pushing member to intermittently compress and release the urethra by means of the pushing member, the urinary pumping device further comprising a control unit configured to control the drive such that a periodic compression and release of the urethra is generatable by the pushing member at a predefined frequency and, optionally, a predefined amplitude, a predefined pressure, a predefined force and/or a predefined duty cycle.

2. The urinary pumping device of claim 1, wherein the activation arrangement is mounted to the toilet seat through an auxiliary structure.

3. The urinary pumping device of claim 1, wherein the pushing member is configured to press the urethra's neighbouring tissue at a specific frequency and at a specific location to compress and release the urethra of the patient so that said urinary pumping device operate as an impedance pump.

4. The urinary pumping device of claim 1, wherein the predefined frequency is in a range of about 1 Hz to about 50 Hz.

5. A urinary pumping device for generating a fluid flow through an urethra of a patient, the urinary pumping device comprising a handheld apparatus comprising:

a penis accommodating section, a pushing device and a drive coupled to the pushing device, said pushing device being configured to induce direct intermittent compression and release of the urethra by physically pressing urethra's neighbouring tissue, the pushing device comprising a pushing member extending out of the handheld apparatus at the penis accommodating section, wherein the penis accommodating section is configured to position the pushing member on the penis of the patient such that the urethra of the patient is intermittently compressible and releasable by means of the pushing member, the urinary pumping device comprising a control unit configured to control the drive such that a periodic compression and release of the urethra is generated by the pushing member at a predefined frequency and, optionally, a predefined amplitude, a predefined pressure, a predefined force and/or a predefined duty cycle.

6. The urinary pumping device of claim 5, wherein the pushing device comprises a surrounding portion dimensioned to be arranged around a penis of the patient.

7. The urinary pumping device of claim 6, wherein the pushing device comprises a diameter adjuster configured to reduce a diameter of the surrounding portion when being arranged around the penis of the patient.

8. The urinary pumping device of claim 7, wherein the surrounding portion of the pushing device has a recess interrupting the surrounding portion in a circumference and the diameter adjuster of the pushing device is configured to change the circumferential extension of the recess.

9. The urinary pumping device of claim 8, wherein the diameter adjuster of the pushing device comprises a lever pivotably mounted to the surrounding portion at one side of the recess and connected to the other side of the recess.

10. The urinary pumping device of claim 6, wherein the surrounding portion of the pushing device comprises a ring portion.

11. The urinary pumping device of claim 6, wherein the surrounding portion of the pushing device comprises a dimension variable polymeric material that exhibits a change of a diameter of the surrounding portion when stimulated.

12. The urinary pumping device of claim 5, wherein the handheld apparatus comprises a finger accommodation section configured to accommodate at least one finger of the patient when another finger of the patient pushes the penis of the patient to the penis accommodation section.

13. The urinary pumping device of claim 5, wherein the predefined frequency is in a range of about 1 Hz to about 50 Hz.

14. The urinary pumping device of claim 5, wherein the pushing member is configured to press the urethra's neighbouring tissue at a specific frequency and at a specific location to compress and release the urethra of the patient so that said urinary pumping device operates as an impedance pump.

15. A urinary pumping device for generating a fluid flow through an urethra of a patient, the urinary pumping device comprising a plug dimensioned to be arranged in a vagina of the patient, said plug comprising:

a pushing member and a drive coupled to the pushing member, said plug being configured to induce direct intermittent compression and release of the urethra by physically pressing urethra's neighbouring tissue, wherein the plug is configured to position the pushing member in the vagina of the patient such that the urethra of the patient is intermittently compressible and releasable by means of the pushing member, the urinary pumping device comprising a control unit configured to control the drive such that a periodic compression and release of the urethra is generated by the pushing member at a predefined frequency.

16. The urinary pumping device of claim 15, wherein the plug comprises a plug adjuster configured to vary a diameter of the plug when being arranged in the vagina of the patient.

17. The urinary pumping device of claim 15, wherein the plug comprises a dimension variable material that exhibits a change of a diameter of the plug when stimulated.

18. The urinary pumping device of claim 17, wherein the dimension variable material of the plug is a polymeric material.

19. The urinary pumping device of claim 15, wherein the pushing member is configured to press a vaginal wall of the patient towards the urethra against the pubic bone.

20. The urinary pumping device of claim 15, wherein the pushing member is configured to press the urethra's neighbouring tissue at a specific frequency and at a specific location to compress and release the urethra of the patient so that said urinary pumping device operates as an impedance pump.

* * * * *